United States Patent
Jessop et al.

(10) Patent No.: US 11,020,103 B2
(45) Date of Patent: Jun. 1, 2021

(54) CHEEK RETRACTOR DEVICE AND METHOD

(71) Applicant: ULTRADENT PRODUCTS, INC., South Jordan, UT (US)

(72) Inventors: Neil T. Jessop, Sandy, UT (US); Bruce S. McLean, Sandy, UT (US); Craig Hines, Lihue, HI (US)

(73) Assignee: Ultradent Products, Inc., South Jordan, UT (US)

( * ) Notice: Subject to any disclaimer, the term of this patent is extended or adjusted under 35 U.S.C. 154(b) by 197 days.

(21) Appl. No.: 15/905,778

(22) Filed: Feb. 26, 2018

(65) Prior Publication Data

US 2018/0193012 A1 Jul. 12, 2018

Related U.S. Application Data

(63) Continuation of application No. 14/776,867, filed as application No. PCT/US2014/028083 on Mar. 14, 2014, now Pat. No. 9,901,332.

(Continued)

(51) Int. Cl.
*A61B 17/02* (2006.01)
*A61C 5/90* (2017.01)
(Continued)

(52) U.S. Cl.
CPC ............ *A61B 17/0293* (2013.01); *A61B 1/24* (2013.01); *A61B 1/32* (2013.01); *A61B 13/00* (2013.01);
(Continued)

(58) Field of Classification Search
CPC .... A61C 5/90; A61C 5/82; A61C 5/14; A61B 17/0293; A61B 17/02; A61B 1/24;
(Continued)

(56) References Cited

U.S. PATENT DOCUMENTS

| 4,820,155 A | 4/1989 | Sauveur |
| 5,037,298 A | 8/1991 | Hickham |

(Continued)

FOREIGN PATENT DOCUMENTS

| CN | 101299956 | 11/2008 |
| KR | 1020100099098 | 9/2010 |
| WO | 2014143911 | 9/2014 |

OTHER PUBLICATIONS

International Search Report, as issued in connection with International Patent Application No. PCT/US2014/028083, dated Jul. 3, 2014, 3 pgs.

(Continued)

*Primary Examiner* — Jacqueline T Johanas
*Assistant Examiner* — Shannel Nicole Belk
(74) *Attorney, Agent, or Firm* — Maschoff Brennan

(57) ABSTRACT

Cheek retraction devices including an upper frame element configured to bear against and retract soft oral tissue from one or more teeth of an upper dental arch, a lower frame element configured to bear against and retract soft oral tissue from one or more teeth of a lower dental arch. The upper and lower frame elements may each include left and right frame portions wherein the upper and lower left frame portions are joined to one another to form a v-shaped hinge on one side of the frame, while upper and lower right frame portions are joined to one another to form a v-shaped hinge on another side of the frame. The v-shaped hinges on opposed sides permit the upper and lower frame elements to be at least partially folded toward each other. A posterior frame element may be provided extending between the v-shaped hinges.

20 Claims, 11 Drawing Sheets

Related U.S. Application Data

(60) Provisional application No. 61/789,929, filed on Mar. 15, 2013.

(51) Int. Cl.
  *A61B 1/24* (2006.01)
  *A61B 1/32* (2006.01)
  *A61B 13/00* (2006.01)
  *A61B 17/00* (2006.01)

(52) U.S. Cl.
  CPC ............... *A61B 17/02* (2013.01); *A61C 5/90* (2017.02); *A61B 2017/00862* (2013.01); *A61B 2560/0443* (2013.01)

(58) Field of Classification Search
  CPC . A61B 1/32; A61B 13/00; A61B 2017/00862; A61B 2560/0443
  See application file for complete search history.

(56) References Cited

U.S. PATENT DOCUMENTS

| | | | |
|---|---|---|---|
| 5,199,872 A * | 4/1993 | Leal | A61B 1/24 433/136 |
| 6,299,446 B1 * | 10/2001 | Ahlers | A61C 5/82 433/136 |
| D496,995 S | 10/2004 | Dorfman | |
| 6,923,761 B1 * | 8/2005 | Dorfman | A61B 1/24 433/140 |
| 7,300,401 B2 | 11/2007 | Patrickus | |
| 8,376,743 B1 * | 2/2013 | Bukhary | A61B 1/24 433/140 |
| D737,964 S | 9/2015 | Jessop et al. | |
| 9,387,054 B2 | 7/2016 | Hines et al. | |
| 9,901,332 B2 * | 2/2018 | Jessop | A61B 1/24 |
| 10,016,258 B2 * | 7/2018 | Jessop | A61C 5/90 |
| 2002/0022211 A1 | 2/2002 | Horiguchi | |
| 2004/0209225 A1 | 10/2004 | Kilcher et al. | |
| 2005/0227199 A1 | 10/2005 | Patrickus | |
| 2006/0063979 A1 * | 3/2006 | Rosenblood | A61B 1/24 600/237 |
| 2006/0069316 A1 | 3/2006 | Dorfman et al. | |
| 2006/0155171 A1 | 7/2006 | Yang | |
| 2006/0234187 A1 | 10/2006 | Kilcher et al. | |
| 2007/0148619 A1 | 6/2007 | Anderson | |
| 2008/0064001 A1 * | 3/2008 | Dorfman | A61C 5/90 433/29 |
| 2011/0060194 A1 * | 3/2011 | Risto | A61B 1/32 600/210 |
| 2018/0318041 A1 | 11/2018 | Jessop et al. | |

OTHER PUBLICATIONS

International Written Opinion, as issued in connection with International Patent Application No. PCT/US2014/028083, dated Jul. 3, 2014, 7 pgs.
United States Patent and Trademark Office; Office Action dated Sep. 13, 2019 in U.S. Appl. No. 16/030,591; 11 pages.
Communication under Rule 71(3) dated Mar. 5, 2020 in European Patent Application No. 14763277.2.
AU Examination Report dated Nov. 27, 2020 as received in Application 2020200559.

* cited by examiner

CHEEK RETRACTOR DEVICE AND METHOD

CROSS-REFERENCE TO RELATED APPLICATIONS

The present application claims the benefit of U.S. Patent Application Ser. No. 61/789,929, filed Mar. 15, 2013, entitled "CHEEK RETRACTOR DEVICE AND METHOD"; PCT Application PCT/US2014/028083 filed Mar. 14, 2014, entitled "CHEEK RETRACTOR DEVICE AND METHOD"; and U.S. patent application Ser. No. 14/776,867, filed Sep. 15, 2015, entitled "CHEEK RETRACTOR DEVICE AND METHOD" the disclosures of which are incorporated by reference in their entireties.

BACKGROUND

1. The Field of the Invention

The present invention is in the field of dentistry, particularly cheek retractor devices for use in isolating a patient's teeth and enlarging the working field for the practitioner.

2. The Relevant Technology

In certain procedures, particularly certain dental procedures, it can be helpful to retract soft oral tissue around the oral cavity, isolating these soft oral tissues (e.g., the cheeks and lips) so as to create an enlarged working field around the teeth and dental arches.

Various retraction devices exist, although these devices share certain problems. They are often difficult to insert and remove, often requiring extensive time to insert and causing discomfort to the patient during insertion and removal. They generally require that a dentist, dental assistant, or other practitioner use both hands to insert and remove the devices. They are generally uncomfortable to patients and can activate patient's pharyngeal reflexes (i.e., gag reflex). As such, it would be beneficial to provide a cheek retraction device exhibiting improved characteristics.

BRIEF SUMMARY

The present invention is directed to cheek retraction devices for use in dental procedures or other procedures requiring access to the oral cavity. Various features are disclosed which may provide collapsibility, ability to latch in a collapsed configuration, and easier insertion into a patient's mouth, (e.g., even allowing insertion with one hand). The device may include structural and/or curvature characteristics which help "pull" the device into a patient's mouth, facilitating easier insertion and maintenance within the mouth once installed.

In an aspect, the cheek retraction device includes a selectively collapsible and expandable frame for insertion into an oral cavity. The collapsed configuration facilitates insertion into the oral cavity, while the expanded configuration while positioned in the oral cavity allows it to bear against and retract soft oral tissue so as to isolate one or more teeth from soft oral tissue and create an enlarged working field. The frame may include an upper frame element configured to bear against and retract soft oral tissue from one or more teeth of an upper dental arch when the frame is in an expanded configuration. Similarly, a lower frame element may be configured to bear against and retract soft oral tissue from one or more teeth of a lower dental arch when the frame is expanded. The upper and lower frame elements may each include left and right frame portions, wherein the upper and lower left frame portions are joined to one another to form a v-shaped hinge on one side of the frame, while the upper and lower right frame portions are joined to one another to form a v-shaped hinge on another side of the frame. The v-shaped hinges on opposed sides (and disposed at a posterior portion of the device) permit the upper and lower frame elements to be at least partially folded toward each other. A posterior width of the upper and lower frame elements as defined between the right and left frame portions adjacent the v-shaped hinges may be greater than an anterior width of the upper and lower frame elements.

Such a configuration provides a greater posterior width to the device than its anterior width, helping to pull the device into the oral cavity, rather than push it out. For example, other cheek retractors exhibit an oppositely configured wedge relationship, where the anterior dimensions of the device are greater than the posterior dimensions. Such configurations exhibit a tendency to be easily pushed out of the oral cavity, rather than maintained in the desired position.

In another aspect, the invention is directed to a cheek retractor device including a selectively collapsible and expandable frame for insertion into an oral cavity. The collapsed configuration facilitates insertion into the oral cavity, while the expanded configuration while positioned in the oral cavity allows it to bear against and retract soft oral tissue so as to isolate one or more teeth from soft oral tissue and create an enlarged working field. The frame may include an upper frame element configured to bear against and retract soft oral tissue from one or more teeth of an upper dental arch when the frame is in an expanded configuration. Similarly, a lower frame element may be configured to bear against and retract soft oral tissue from one or more teeth of a lower dental arch when the frame is expanded. The upper and lower frame elements may each include left and right frame portions wherein the upper and lower left frame portions are joined to one another to form a v-shaped hinge on one side of the frame, while the upper and lower right frame portions are joined to one another to form a v-shaped hinge on another side of the frame. The v-shaped hinges on opposed sides (and disposed at a posterior portion of the device) permit the upper and lower frame elements to be at least partially folded toward each other. A posterior frame element may be provided extending between the v-shaped hinges. The posterior frame element may include a v-shaped or u-shaped portion to permit the v-shaped hinges on opposed posterior sides of the frame to be at least partially collapsed towards one another so that the device is collapsible in a side-to-side dimension as well as an upper-to-lower dimension.

In another aspect, the invention is directed to a cheek retractor device including a selectively collapsible and expandable frame for insertion into an oral cavity. The collapsed configuration facilitates insertion into the oral cavity, while the expanded configuration while positioned in the oral cavity allows it to bear against and retract soft oral tissue so as to isolate one or more teeth from soft oral tissue and create an enlarged working field. The frame may include an upper frame element configured to bear against and retract soft oral tissue from one or more teeth of an upper dental arch when the frame is in an expanded configuration. Similarly, a lower frame element may be configured to bear against and retract soft oral tissue from one or more teeth of a lower dental arch when the frame is expanded. The upper and lower frame elements may each include left and right frame portions wherein the upper and lower left frame portions are joined to one another to form a v-shaped hinge on one side of the frame, while the upper and lower right frame portions are joined to one another to form a v-shaped hinge on another side of the frame. The v-shaped hinges on opposed sides (and disposed at a posterior portion of the device) permit the upper and lower frame elements to be at least partially folded toward each other. The frame may include an upper lip protecting member disposed on an anterior portion of the upper frame element that is configured to extend away from an oral cavity and over an upper lip. A lower lip protecting member may similarly be disposed on an anterior portion of the lower frame element in a manner to extend away from the oral cavity and over a lower lip. The lip protecting members may be selectively engagable with one another when the upper frame element is folded towards the lower frame element so as to latch the upper and lower frame elements together.

In another aspect, the invention is directed to a cheek retractor device including a selectively collapsible and expandable frame for insertion into an oral cavity. The collapsed configuration facilitates insertion into the oral cavity, while the expanded configuration while positioned in the oral cavity allows it to bear against and retract soft oral tissue so as to isolate one or more teeth from soft oral tissue and create an enlarged working field. The frame may include an upper frame element configured to bear against and retract soft oral tissue from one or more teeth of an upper dental arch when the frame is in an expanded configuration. Similarly, a lower frame element may be configured to bear against and retract soft oral tissue from one or more teeth of a lower dental arch when the frame is expanded. The upper and lower frame elements may each include left and right frame portions wherein the upper and lower left frame portions are joined to one another to form a v-shaped hinge on one side of the frame, while the upper and lower right frame portions are joined to one another to form a v-shaped hinge on another side of the frame. The v-shaped hinges on opposed sides (and disposed at a posterior portion of the device) permit the upper and lower frame elements to be at least partially folded toward each other. A posterior frame element may extend between the v-shaped hinges on opposed sides of the frame, and a selectively removable tongue guard may be provided that is selectively couplable to the posterior frame element to allow attachment or removal of the tongue guard.

These and other benefits, advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

I Introduction

The invention generally relates to cheek retractor devices useful for isolating one or more teeth from soft oral tissue and creating an enlarged working field. Such cheek retractor devices may include a selectively collapsible and expandable frame for insertion into an oral cavity. The collapsed configuration facilitates insertion into the oral cavity, while the expanded configuration, while positioned in the oral cavity, allows the frame to bear against and retract soft oral tissue so as to isolate one or more teeth from soft oral tissue and create an enlarged working field.

The frame may include an upper frame element configured to bear against and retract soft oral tissue from one or more teeth of an upper dental arch when the frame is in an expanded configuration. Similarly, a lower frame element may be configured to bear against and retract soft oral tissue from one or more teeth of a lower dental arch when the frame is expanded. The upper and lower frame elements may each include left and right frame portions wherein the upper and lower left frame portions are joined to one another to form a v-shaped hinge on one side of the frame, while the upper and lower right frame portions are joined to one another to form a v-shaped hinge on another side of the frame. The v-shaped hinges on opposed sides (and disposed at a posterior portion of the device) permit the upper and lower frame elements to be at least partially folded toward each other. A posterior frame element may be provided extending between the v-shaped hinges.

II Exemplary Cheek Retraction Devices

Figure 1:
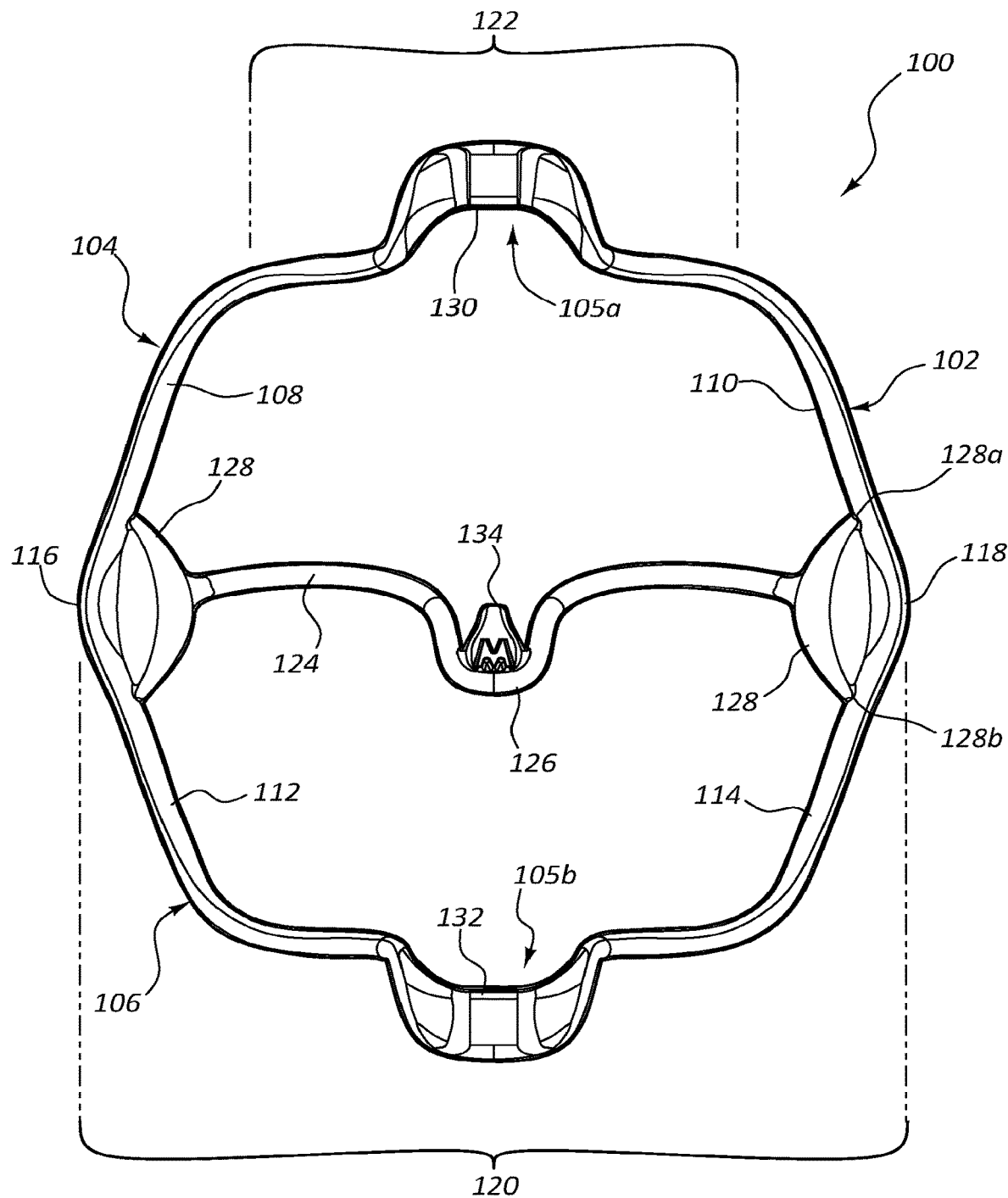
FIG. 1 is an anterior or front view of an exemplary cheek retractor device.
Figure 2:
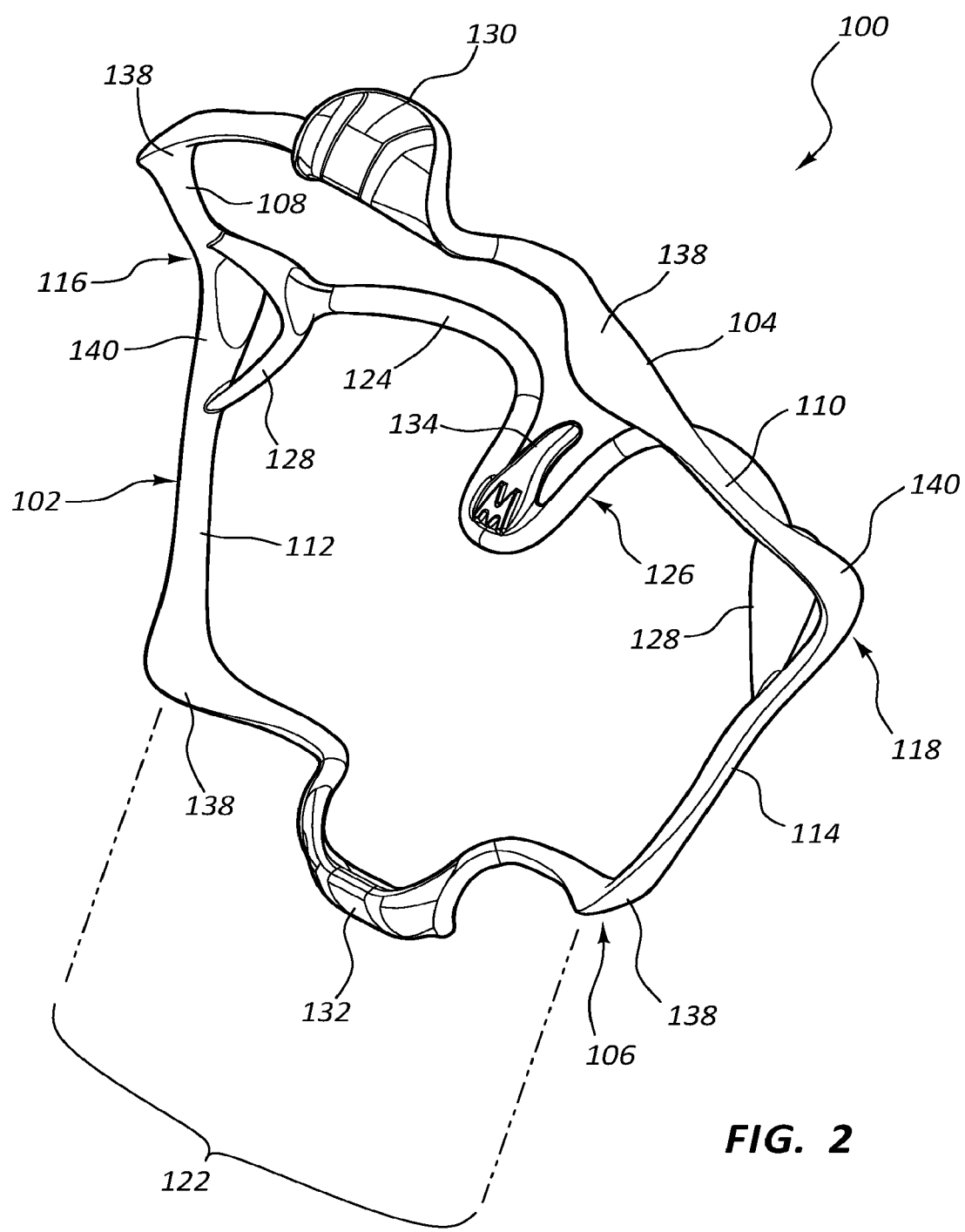
FIG. 2 is a perspective view of the device of FIG. 1.

FIGS. 1 through 5 illustrate an exemplary cheek retraction device 100. FIG. 1, for example, shows a cheek retractor device 100 comprising a frame 102 for insertion into an oral cavity. The frame 102 is selectively collapsible and expandable. In a collapsed configuration (e.g., see FIG. 3), device 100 is more easily inserted into the oral cavity, while the expanded configuration (e.g., see FIG. 5) allows frame 102 to bear against and retract soft oral tissue from adjacent teeth to create an enlarged working field for the practitioner. The frame 102 may be flexible yet resilient. For example, absent any applied forces (or engagement of a latching mechanism), frame 102 may assume the expanded configuration seen in FIGS. 1-4.

The frame may include an upper frame element 104 and a lower frame element 106. During use, the upper frame element 104 may bear against and retract soft oral tissue from one or more teeth of a patient's upper dental arch, while the lower frame element 106 may bear against and retract soft oral tissue from one or more teeth of a patient's lower dental arch. Upper frame element 104 may include left frame portion 108 and right frame portion 110. Similarly, lower frame element 106 may include left frame portion 112 and right frame portion 114. Such right and left references are made from the perspective of the practitioner facing the patient in whom the device is to be inserted, although it is to be understood that the designation is somewhat arbitrary, and the frame of reference could alternatively be made from the perspective of the patient (i.e., right becomes left and vice versa).

The upper and lower left frame portions 108 and 112, respectively, may be joined to one another to form a v-shaped hinge 116 on one side of the frame 102. In a similar manner, upper and lower right frame portions 110 and 114, respectively may be joined to one another to form another v-shaped hinge 118 on another side of frame 102. V-shaped hinges 116 and 118 permit upper and lower frame elements 104 and 106 to be at least partially folded toward each other. While hinges 116 and 118 are generally described as "v-shaped", this term is to be construed broadly, such that any acute angular relationship between the upper and lower left or right frame portions (e.g., 108, 112 or 110, 114) may be considered v-shaped. As such, u-shaped and other similar structures are encompassed within the meaning of "v-shaped", as the term is used herein, such that the term "v-shaped" is used for simplicity.

In an embodiment, a posterior width 120 of upper 104 and lower 106 frame elements as defined between the right and left frame portions adjacent v-shaped hinges 116, 118 (e.g., the width from a vertex of angled hinge 116 to the vertex of angled hinge 118) is greater than an anterior width 122 of the upper 104 and lower 106 frame elements. For example, a posterior width 120 may be measured from the vertex of left hinge 116 to the vertex of the right hinge 118. Anterior width 122, for example, may be measured as that portion that is generally horizontal, before bending towards hinges 116, 118. Although different sizes of the device 100 may be designed depending on the facial anatomy of the patient (which may be determined, for example, by the spacing between the eyes), one embodiment of the device 100 may have a posterior width 120 from about 110-130 mm (e.g., 115-120 mm) and an anterior width 122 from about 80-90 mm (e.g., about 85 mm). In an embodiment, the posterior width 120 may be about 20% to about 80%, from about 25% to about 75%, or from about 30% to about 50% (e.g., about 40%) greater than anterior width 122.

Such a larger posterior width 120 or posteriorly, outwardly curved or flared structure provides a configuration by which the device tends to pull itself into the patient's mouth and be retained there, as opposed to exhibiting a tendency for the cheek retractor to be pushed out of the patient's mouth, which is typical of many existing devices. In addition, this feature helps improve the ease of insertion of device 100.

Frame 102 may also include a posterior frame element 124 extending between v-shaped hinges 116, 118. Posterior frame element 124 may include a v-shaped or u-shaped portion 126 (e.g., centrally located along element 124) to permit the v-shaped hinges 116, 118 on opposed posterior sides of the frame 102 to be at least partially collapsible towards one another so that the cheek retraction device 100 is collapsible in a side-to-side dimension as well as an upper-to-lower dimension. Such two-dimensional collapsibility greatly improves the ease of insertion, facilitating single-handed insertion and installation.

Posterior frame element 124 may be connected on either side to upper frame element 104 and lower frame element 106 by floating gussets 128 providing a pair of connections bridging the v-shaped hinges. For example, right floating gusset 128 may connect with upper right frame portion 110 at 128a, and with lower right frame portion 114 at 128b. The left floating gusset 128 may be similarly connected. Floating gussets 128 may provide additional rigidity (e.g., it may be a rigid element) that helps provide outward curvature to frame 102, and directs applied collapsing forces in an upper-lower direction, stabilizing the structure as it is collapsed downward. Floating gusset 128 may also facilitate easier side-to-side collapsibility when applying side to side forces, as posterior frame element 124 is not directly connected to upper and lower frame elements at hinges 116, 118, but at points spaced apart from the hinges.

Device 100 may include upper and lower lip protecting members 130 and 132, respectively. Upper lip protecting member 130 may be centrally disposed on the anterior portion of upper frame element 104, such that lip protecting member 130 extends away from the patient's oral cavity and over the patient's upper lip. Lower lip protecting member 132 may be similarly disposed along lower frame element 106 so as to extend away from the patient's oral cavity and over the patient's lower lip.

Lip protecting members 130 and 132 may curve over and protect the patient's lips to during a dental procedure. In addition, as perhaps best seen in FIG. 1, members 130 and 132 may provide troughs 105a and 105b above and below the generally horizontal anterior line defined by the other anterior portions of upper and lower frame elements 104 and 106 or serve to enlarge the working field. Such troughs may further enlarge the working field available to the practitioner in the region of the patient's incisors, while at the same time covering and protecting the central portion of the patient's lips. In an embodiment, lip protecting members 130 and 132 may be made from a stiffer material than the other frame portions of device 100, which are relatively flexible and resilient. In addition to the benefits described above, lip protection members 130 and 132 may also serve as an emergency removal handle should the device need to be removed quickly. Even where quick removal may not be needed, lip protection members may present a portion of structure 100 that may be easily and readily grasped by the practitioner when the device is to be removed.

Figure 3:
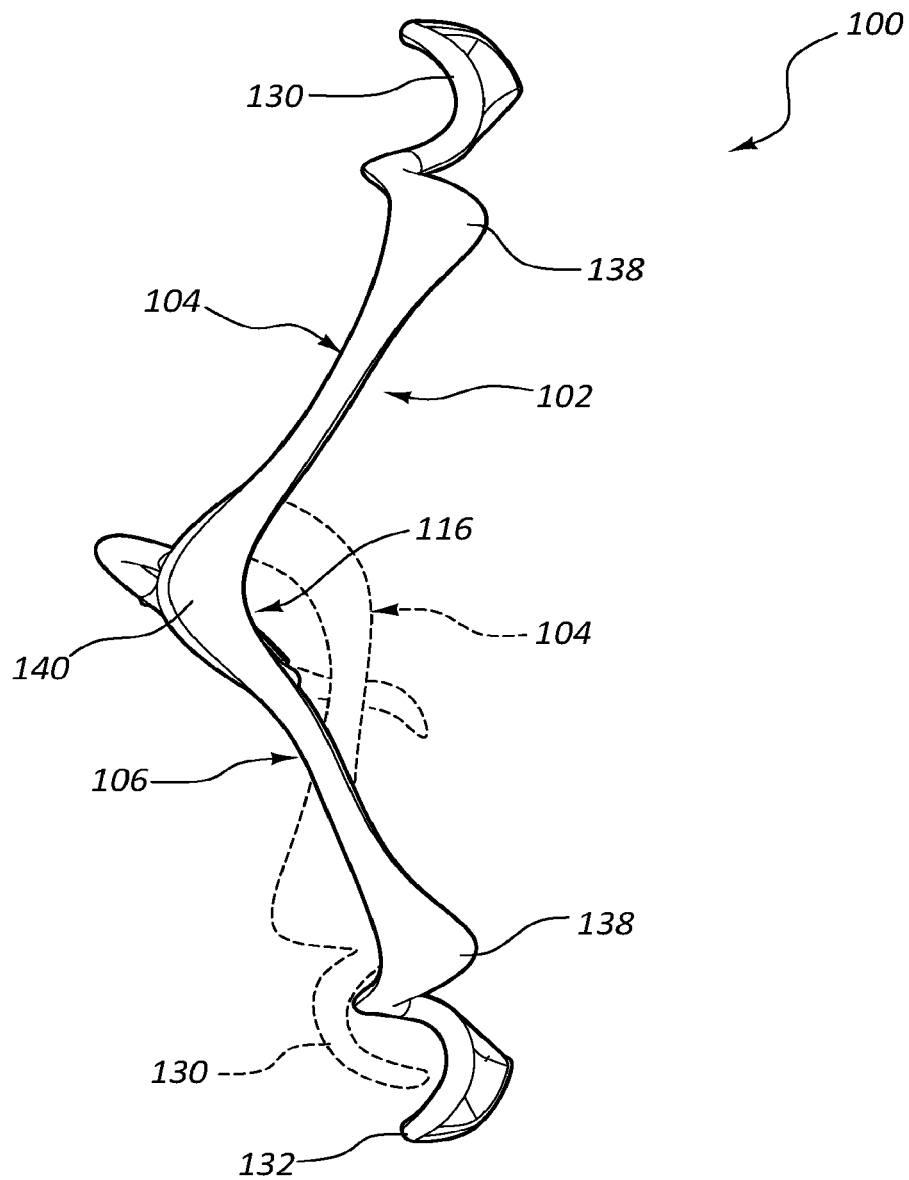
FIG. 3 is a side view of the device of FIG. 1, with the upper frame element also shown in broken lines showing how it may be folded and latched with the lower frame member.
Figure 4:
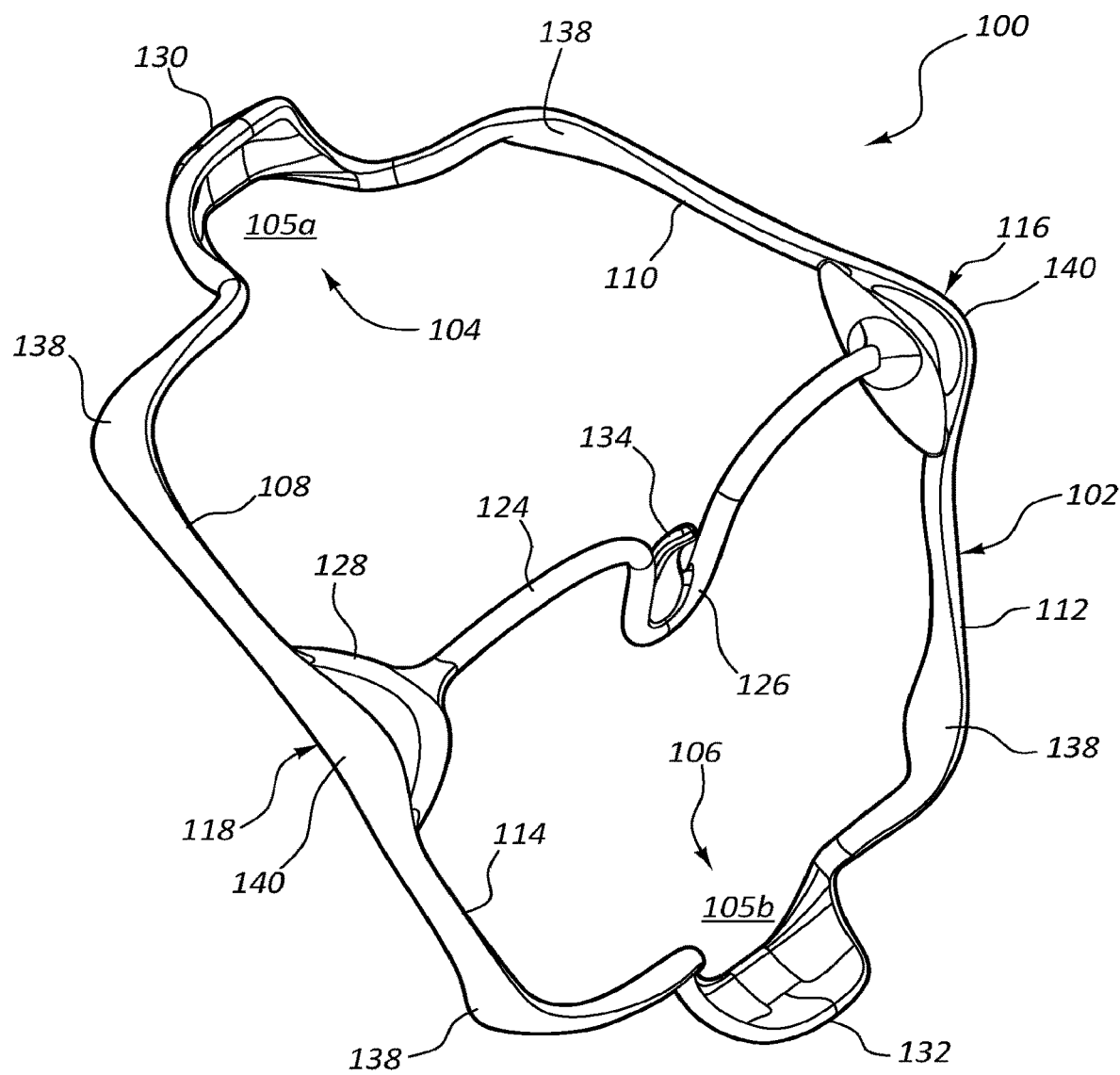
FIG. 4 is a posterior or rear perspective view of the device of FIG. 1.
Figure 5:
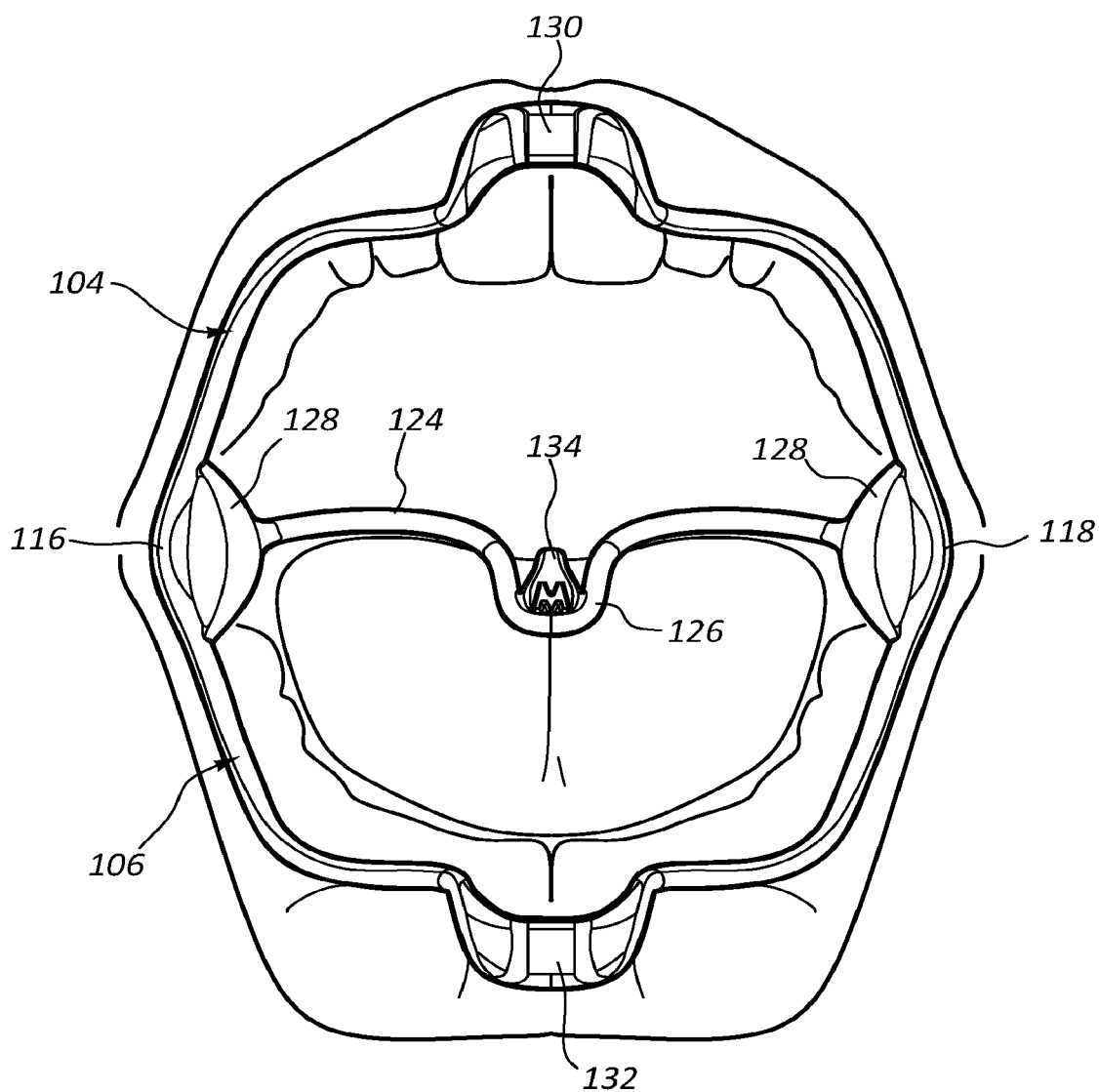
FIG. 5 is an anterior or front view of the device of FIG. 1 installed within the oral cavity of a patient.
Figure 6:
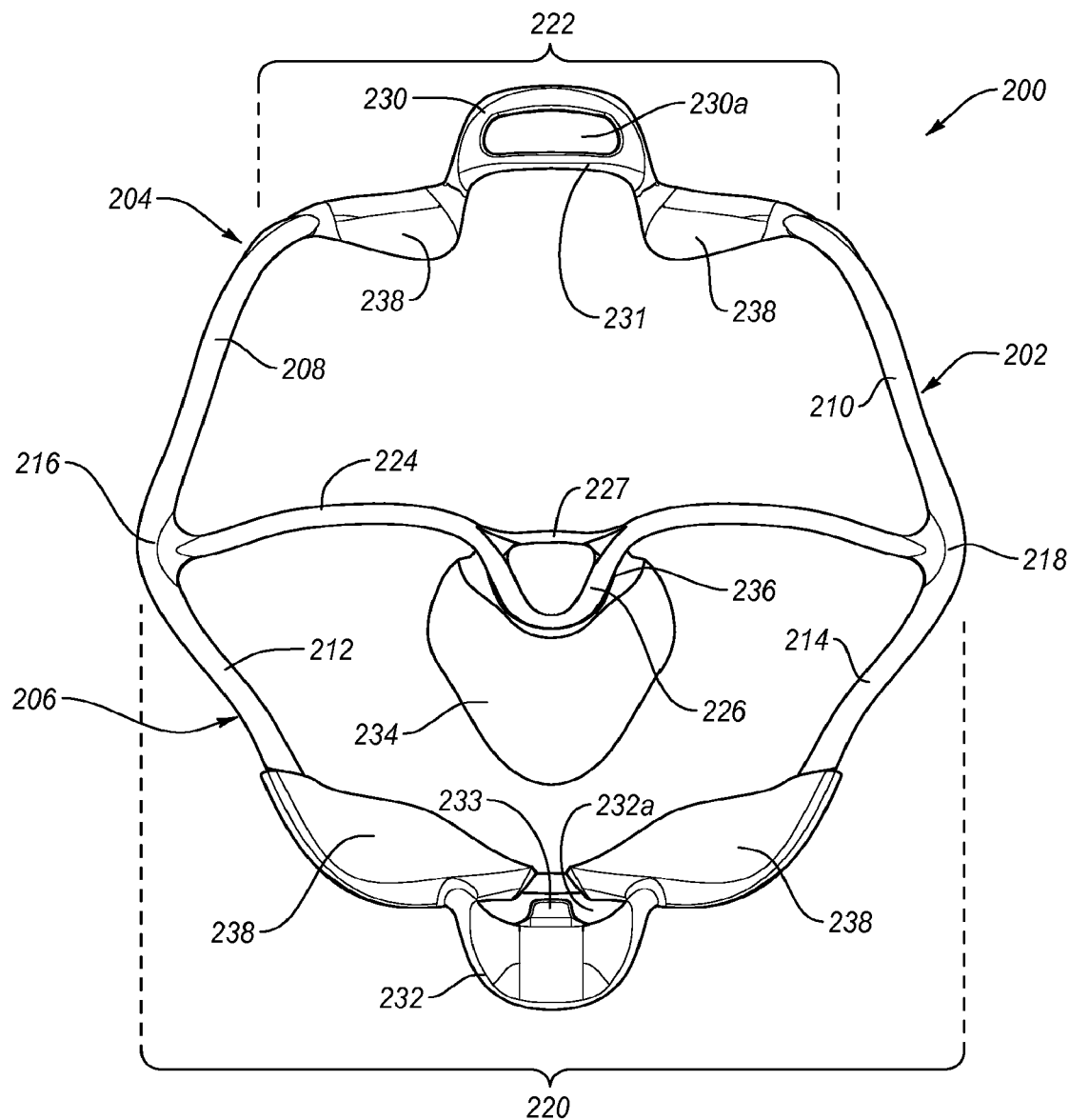
FIG. 6 is an anterior or front view of an alternative exemplary cheek retractor device.
Figure 7:
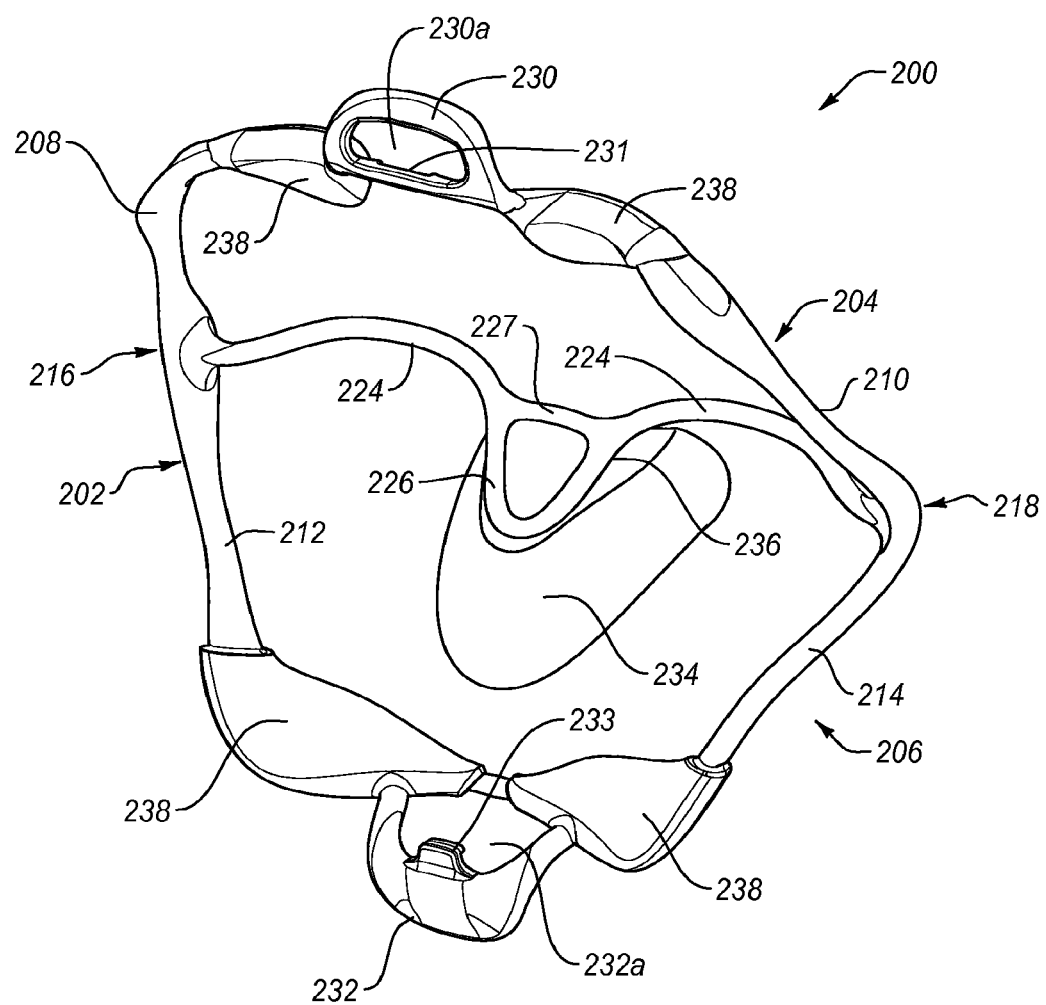
FIG. 7 is a perspective view of the device of FIG. 6.

Furthermore, as perhaps best seen in FIG. 3, the lip protecting members 130 and 132 may be selectively engagable with one another when the upper frame element 104 is folded towards the lower frame element 106 so as to latch the upper 104 and lower 106 frame elements together. Of course, while sometimes described herein in terms of the upper frame element being folded downward towards lower frame element 106, it will be understood that the one or both frame elements may move during such folding so that lower frame element 106 may similarly be folded toward upper frame element 104.

An example of such folding and latching is illustrated in FIG. 3, where the device is shown both before folding (in solid lines), and after folding (with the upper frame element 104 shown again in broken lines). Such a latching mechanism may be used to lock the frame 102 in a closed, collapsed position prior to insertion into the patient's mouth. As a result of the device being latched in a configuration where it is collapsed in the upper-to-lower dimension, the practitioner is not required to hold the device in this collapsed configuration (it may be maintained until released), allowing the practitioner to more easily hold the device in a side-to-side collapsed configuration as well during insertion. Once cheek retractor device 100 is inserted into the patient's mouth, the latch mechanism may be released to expand within the patient's mouth. For example, if the upper 104 and lower 106 frame elements are latched together, a practitioner may use one hand to squeeze the device together in a side to side manner, and insertion may be easily done with one hand, if such insertion is desired. Of course, two-handed insertion is also possible. Different mechanisms for latching upper and lower frame elements 104 and 106 (e.g., a latch structure separate from any lip protection members) may alternatively or additionally be provided. Such additional latch structure could also be provided for latching any side-to-side consolidation of device 100, as well.

Device 100 may also include a tongue guard 134, which may be selectively removable. For example, this may allow attachment or removal of tongue guard 134 from posterior element 124, even while device 100 is installed within an oral cavity of a patient. While tongue guard 134 may be removed while device 100 is installed within an oral cavity of a patient, it may also be removed prior to insertion, after insertion or removal, or at any point in the procedure. Tongue guard 134 may be coupleable to posterior frame element 134 through any suitable mechanism (e.g., friction fit, press-fit, keyed coupling, etc.). For example, a protrusion and receptacle configuration shared between tongue guard and posterior frame element 134 may allow tongue guard 134 to "click" into place once seated.

Tongue guard 134 may serve to prevent activation of a patient's pharyngeal reflexes (i.e., gag reflex). In some patients with a sensitive or "strong" pharyngeal reflex, it may be desirable to remove tongue guard 134 from the device 100. A removable tongue guard 134 permits the device 100 to be used with or without tongue guard 134, depending on patient need or preference. In an embodiment, aspiration may be provided through tongue guard 134 (e.g., it may include perforations or holes formed therethrough). Tongue guard 134 may be formed of the same or a different material than the other portions of device 100. For example, a material that is particularly flexible, soft and adaptable (e.g., silicone or a thermoplastic elastomer) may be preferred. Tongue guard 134 may partially or substantially fully encapsulate or envelop at least a portion of the tongue, such as the distal end of the tongue. Tongue guard 134 may advantageously be supported on posterior frame element 124 which may include a wire frame that permits it to move somewhat from side to side as frame element 124 is deformed (e.g., to allow the patient some ability to move the tongue during a procedure). In addition, the presence of floating gussets 128 as described may cause tongue guard 134 and v-shaped or u-shaped portion 126 of posterior frame element 124 to push forward as device 100 is collapsed and backward as device 100 is expanded.

Device 100 may also include one or more bumpers or enlarged portions on frame 102, positioned to provide additional cushioning to specific areas of the oral cavity. For example, a pair of anterior bumpers 138 on each of the upper and lower frame members may be provided. In addition, left and right posterior bumpers 140 may be provided on frame 102 adjacent v-shaped hinges 116 and 118. Bumpers 138 and 140 may comprise enlarged portions of frame 102 as compared to adjacent portions of the frame 102, to increase surface area contact with soft tissues in these regions, providing increased comfort as the bumpers 138, 140 bear against soft oral tissue. The bumpers may also provide improved access to the oral cavity by the practitioner, better holding back adjacent soft tissue.

For example, anterior bumpers 138 may be located at or near the portion of the upper left and right frame portions where upper frame element 104 bends posteriorly in order to connect with v-shaped hinges 116 and 118. The anterior bumpers 138 of the lower frame element may be similarly disposed so that the upper and lower anterior bumpers 138 serve to cushion the anterior cheek soft tissue adjacent the ends of the patient's mouth. The posterior bumpers 140 similarly serve to cushion the posterior cheek soft tissue towards the back of the patient's mouth, adjacent the jaw.

For example, many existing retraction devices tend to uncomfortably "grab" the corners of the patient's mouth. Bumpers 138 aid in reducing or eliminating any such tendency, greatly increasing the comfort of the device as compared to available alternatives.

FIGS. 6 through 11 illustrate another exemplary cheek retraction device 200, similar to device 100. Device 200 similarly includes a frame 202 that is selectively collapsible and expandable. Frame 202 may include an upper frame element 204, which may bear against and retract cheeks and/or lips from teeth of the upper dental arch, and a lower frame element 206, which retracts cheeks and/or lips from teeth of the lower dental arch. Upper frame element 204 may include left frame portion 208 and right frame portion 210. Similarly, lower frame element 206 may include left frame portion 212 and right frame portion 214. Frame portions 208 and 212 may be joined to one another to form a v-shaped hinge 216, and right frame portions 210 and 214, may be joined to one another to form another v-shaped hinge 218 on an opposite side of frame 202.

As with device 100, a posterior width 220 of upper 204 and lower 206 frame elements as defined between the right and left frame portions adjacent v-shaped hinges 216, 218 (e.g., the width from a vertex of angled hinge 216 to the vertex of angled hinge 218) may be greater than an anterior width 222 of the upper 204 and lower 206 frame elements. Also similar to device 100, frame 202 may also include a posterior frame element 224 extending between v-shaped hinges 216, 218. Posterior frame element 224 may include a v-shaped or u-shaped portion 226 (e.g., centrally located along element 224) to facilitate side-to-side collapsibility of device 200. As shown, a cross-member portion 227 of element 224 may extend between the ends of v or u-shaped portion 226 (e.g., providing a triangular shaped portion in member 224). The v-shaped or u-shaped portion 226 and the cross-member portion 227 may function as a tongue guard to aid in restraining or isolating at least a portion of the tongue.

Instead of floating gussets 128, posterior frame element 224 of device 200 may be connected directly to upper and lower frame elements 204 and 206, respectively at the location of hinges 216, 218.

Figure 8:
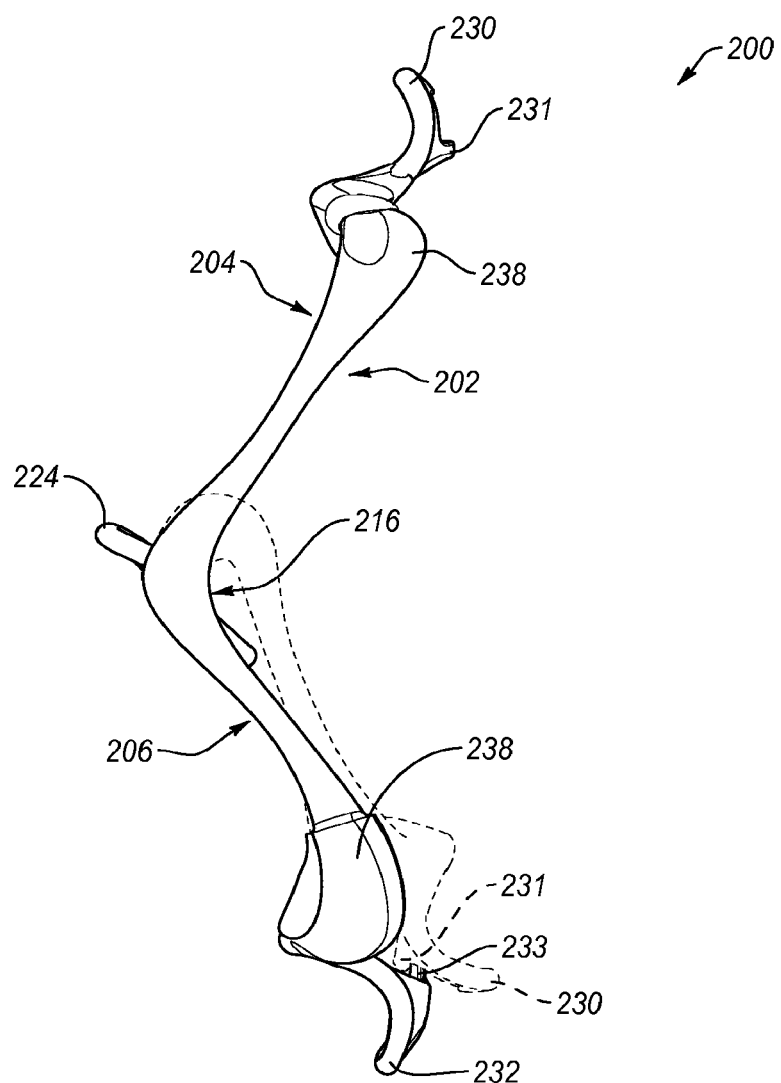
FIG. 8 is a side view of the device of FIG. 6, with the upper frame element also shown in broken lines showing how it may be folded and latched with the lower frame member.
Figure 9:
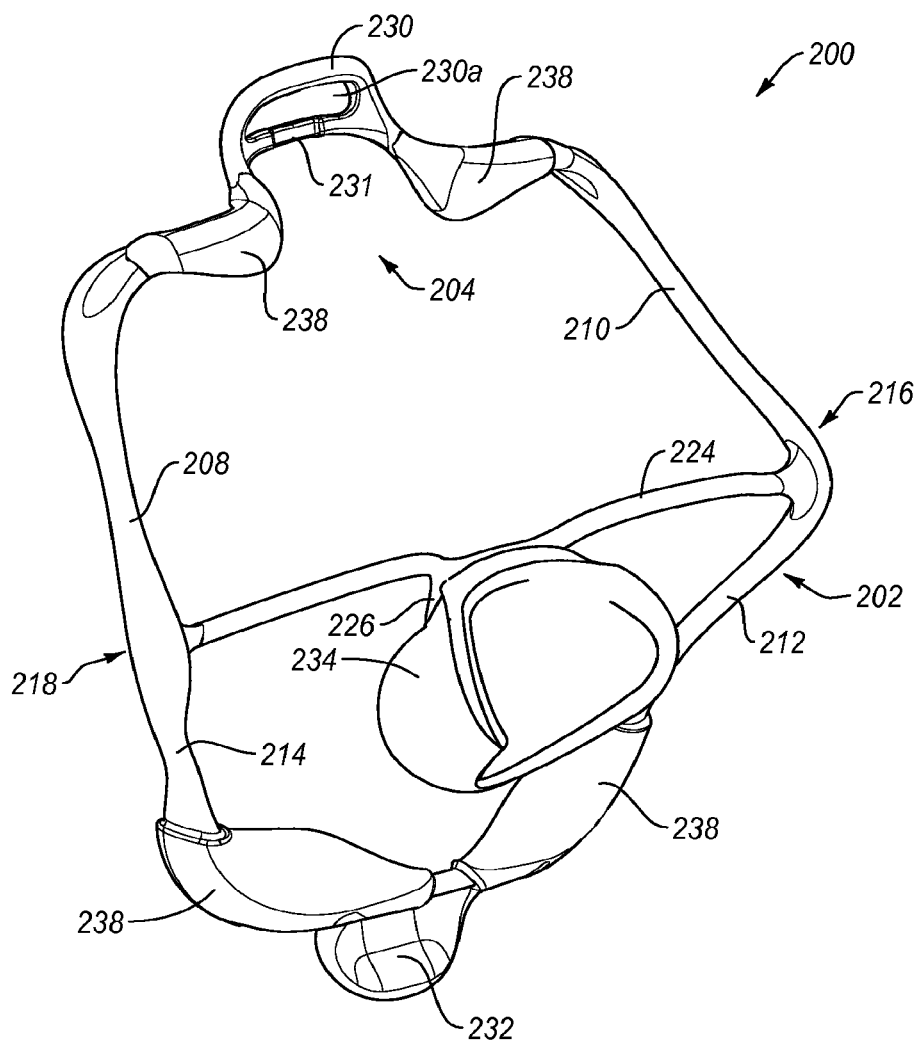
FIG. 9 is a posterior or rear perspective view of the device of FIG. 6.

Illustrated upper and lower lip protecting members 230 and 232 are also somewhat different than those illustrated with device 100. Both members 230, 232 may include a hollow portion 230a, 232a, respectively. Upper lip protecting member 230 may include a cross-member 231 adjacent portion 230a, which may serve to latch with a corresponding latch member 233 of lower lip protecting member 232. As with device 100, lip protecting members 230 and 232 may curve over and protect the patient's lips during a dental procedure, extending outside the patient's mouth. Because of their extension outside of the mouth, they provide a convenient handle that can be gripped when removing or positioning the device. FIG. 8 shows the lip protecting members 230 and 232 selectively engaged with one another, with cross-member 231 latched with latch member 233. For example, cross-member 231 may snap or compression fit under latch member 233, holding cross-member 231, and thus upper frame element 204 latched to lower frame element 206. Tongue guard 234 is not shown in FIG. 8 so as to more clearly show the other structures. As seen in FIG. 8, the side view of the device may be generally L-shaped, as defined by the upper and lower frame elements.

Figure 11:
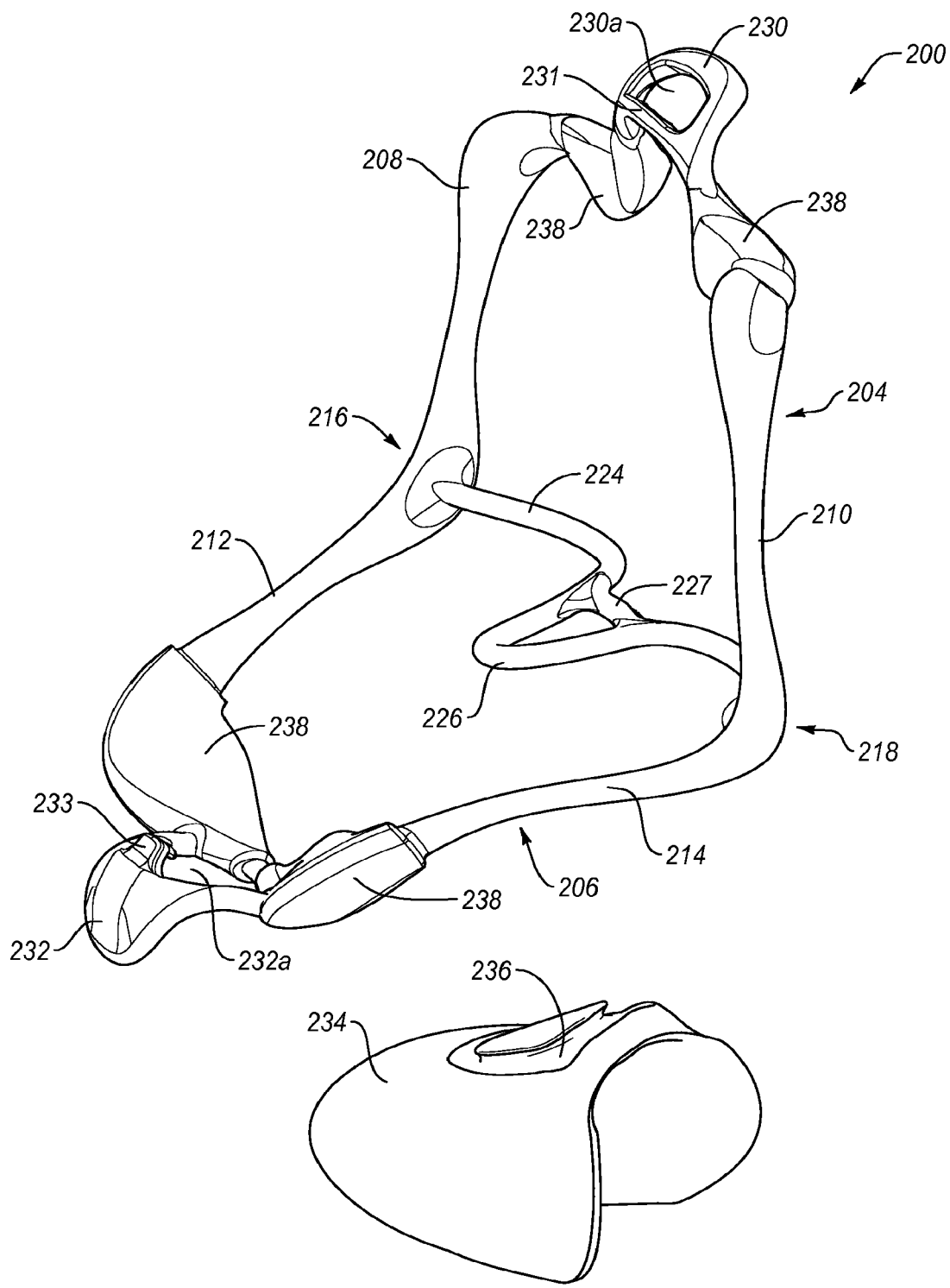
FIG. 11 is a perspective view of the device of FIG. 6, with the tongue garage shown separated from the cheek retractor device.

Device 200 includes a differently configured tongue guard 234 than that of device 100. Tongue guard 234, may be selectively removable (e.g., via a snap-fit compression fit, or similar, as shown in FIG. 11. For example, a top surface of tongue guard 234 may include a recess 236 corresponding to curved portion 226, allowing curved portion 226 to snap into recess 236, attaching tongue guard 234 to frame 202. Tongue guard 234 is further configured as a sheath, which may be closed at the anterior end, and open at the posterior end, so that the tongue may be introduced therein. As such, structure 234 may serve as a garage into which the tongue may be introduced, so as to ensure the tongue does not interfere with practitioner access to the desired areas of the oral cavity, while also protecting the tongue as it is enveloped by guard 234.

Figure 10:
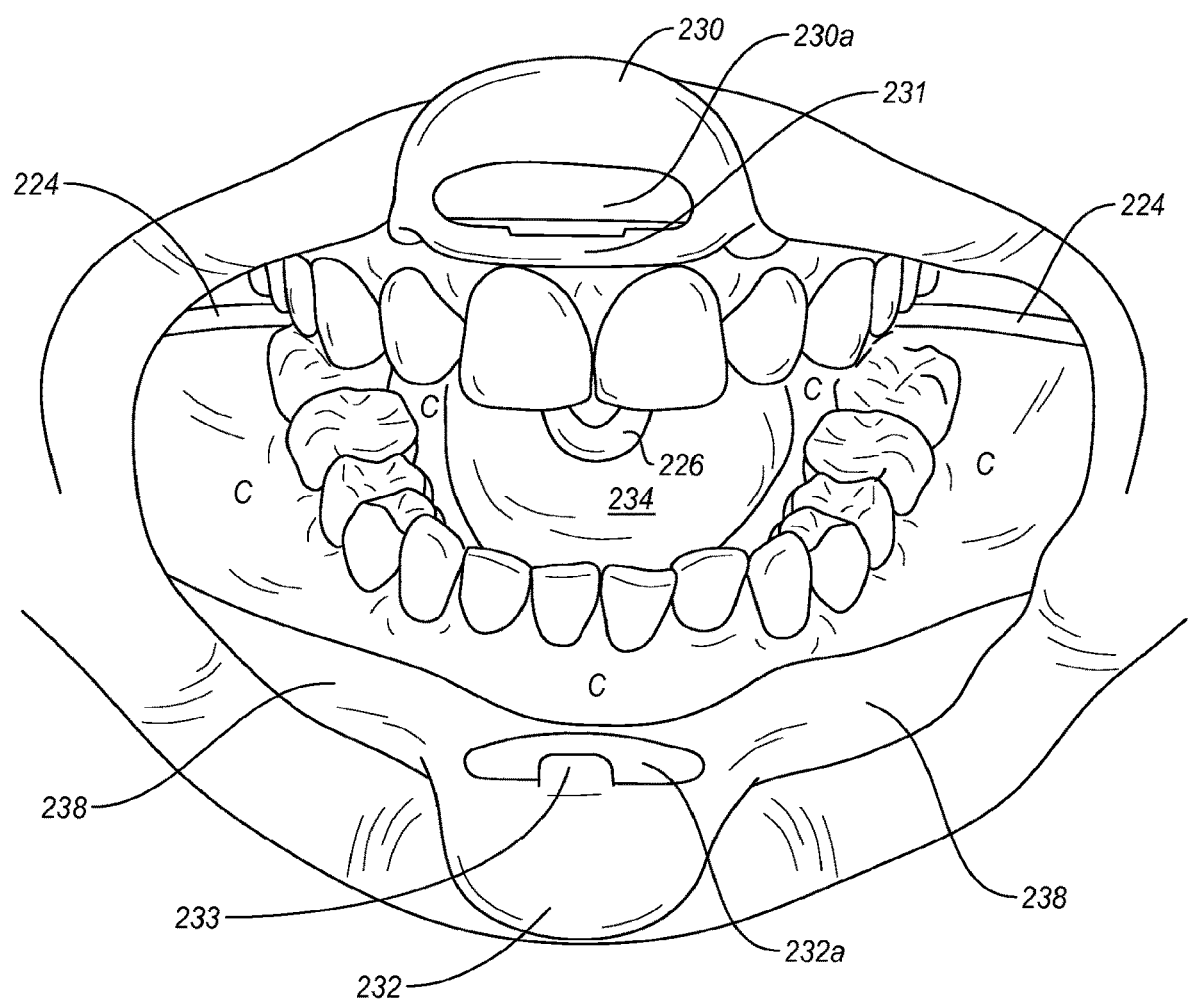
FIG. 10 is an anterior or front view of the device of FIG. 6 installed within the oral cavity of a patient.

When the patient's tongue is received within guard 234, the naturally applied force may push the device 200 forward (e.g., 1-4 mm), causing a further expansion of device 200 within the oral cavity, to create an even greater clearance around the dental arches (i.e., between the dental arches and the cheeks and/or lips, as well as between the tongue (tongue guard 234) and the lingual dental arch surfaces). Clearance provided between the dental arch and the soft tissue of the cheeks and/or lips with the device in place may depend on the particular anatomy of a given patient, but may typically be as much as 2 cm, e.g., at least about 4 mm, at least about 8 mm, at least about 12 mm, etc. FIG. 10 shows a typical clearance (C) around the entire buccal side of lower dental arch of 4 mm to about 2 cm, also showing good clearance on the lingual side of the lower dental arch, between the tongue guard 234 and the dental arch. As seen, the device is able to retract both the lips and the cheeks away from the dental arch, providing excellent clearance all around. Of course, any of the devices according to the present invention may be employed without a tongue guard.

When installed, the device pushes out on the lips and the cheeks simultaneously, retracting these soft tissues away from the dental arches. In that configuration, particularly when employed with a tongue guard such as guard 234, the device "floats" within the mouth, without actually resting on the jaw of the patient. Because of its "floating" configuration, the load applied by the tongue can shift the device as a whole forward (e.g., 1-4 mm), creating somewhat more retraction of the cheeks and lips.

The described retraction devices provide particularly improved retraction adjacent the posterior regions of the dental arch, providing excellent clearance all around the dental arch, including the rear molars, without the device blocking or impeding practitioner access to these areas around the molars.

As with device 100 one or more bumpers 238 or enlarged portions on frame 202 may be provided. In an embodiment, such bumpers 238 may comprise a different material than adjacent frame 202, e.g., comprising a softer, flexible, and/or elastomeric material overmolded with respect to frame 202. For example, bumpers 238 may have a durometer from 0 to about 50, 0 to about 25, or about 15. Tongue guard 234 may similarly be formed of a different material than frame 202, and may have durometer characteristics that are harder than bumpers 238. For example, tongue guard 234 may have a durometer hardness from about 50 to about 100, about 50 to about 90, or about 60 to about 80. Tongue guard may comprise a flexible and/or elastomeric material.

Both devices 100 and 200 advantageously may allow full closure of the patient's mouth, with the device installed. This is a distinct advantage over many existing cheek retractor devices, where full closure of the jaw is not possible. Because closure of the jaw is possible, a practitioner may perform a bite-check without having to remove the device. As illustrated in FIG. 10, the devices 100 and 200 provide excellent displacement or retraction of both the lips and the cheeks, so as to provide a large clearance area (C) around the teeth where the practitioner would like to access. Such clearance provides excellent results for introduction of a dental drill, or for use with an intra-oral scanner, for example, to scan the dental and/or oral structures within the mouth (e.g., for digital crown manufacture). Another advantageous use of the retraction device may be for in-office tooth bleaching. Because the device provides such excellent clearance around the dental arches (i.e., between the dental arch and adjacent soft tissue cheeks and lips, there is less risk of contact between irritative tooth bleaching compositions and such soft tissues, which may otherwise irritate or burn the soft tissues. In addition to allowing full closure of the jaw, the devices according to the present invention may be configured so as to not block or impede practitioner access to the first and second molars of a typical patient. This is advantageous, as some retraction devices do not provide good access to the posterior teeth, particularly the rear molars. For example, the frame members (e.g., 208, 210, 212, 214, 224) may tend to extend bucally, and generally parallel to, and then wrap around the dental arch, behind the rear molars. In addition, as described above, the inclusion of bumpers (e.g., 138, 238) advantageously reduces any tendency of the device to uncomfortably "grab" the corners of the mouth of the patient, providing increased comfort.

According to an embodiment, the frame of any of the embodiments may advantageously be formed of a shape-memory nickel-titanium alloy exhibiting a martensitic transformation temperature between ambient temperature (e.g., about 20° C.) and body temperature (e.g., 37° C.). Such a shape memory alloy could allow the device to be highly deformable at ambient temperature prior to and during insertion, while become rigid as it warms to body temperature. This would be advantageous in practice because the alloy could be flexible and easily deformed before insertion, while still providing excellent retraction after warming up to body temperature. In other embodiments, the frame may be made of any suitable plastic (e.g., polymeric), metal, or other suitable materials. Inexpensive plastic models may be intended for single use, so as to be disposable after a single use. A flexible plastic material for the frame may provide excellent results. Other models, such as one formed of a shape memory nickel-titanium, alloy may be autoclaved or otherwise sanitized following use, so as to allow reuse of the device. In any case, the material is sufficiently flexible so as to allow bending or folding of the upper and lower frame members towards one another, as well as the left and right sides towards one another, and so that when released, the frame is able to recoil back to an expanded configuration.

A device in which the frame is formed of a shape memory nickel-titanium alloy may further include an exterior coating (e.g., silicone, any suitable overmolded plastic, or other coating otherwise encapsulating the Ni—Ti frame) to retard (e.g., insulate) the temperature induced phase transformation of the nickel-titanium alloy. Such a coating may control the rate of heating of the frame after insertion, allowing retraction to occur at a gradual, comfortable and gentle pace.

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A cheek and lip expansion device comprising:
an upper frame element forming a portion of a frame, the upper frame element including a first side, a second side, and an anterior portion disposed between the first side and the second side, the anterior portion including a generally horizontal portion that posteriorly bends, the first side of the upper frame element bending posteriorly, the second side of the upper frame element bending posteriorly;
a lower frame element forming a portion of the frame, the lower frame element including a first side, a second side, and an anterior portion disposed between the first side and the second side, the anterior portion including a generally horizontal portion that posteriorly bends, the first side of the lower frame element bending posteriorly, the second side of the lower frame element bending posteriorly, the first side of the upper frame element posteriorly connected to the first side of the lower frame element, the second side of the upper frame element posteriorly connected to the second side of the lower frame element; and
a posterior frame element extending between a posterior portion of a first side of the frame and a posterior portion of a second side of the frame;
wherein the device is selectively positionable in a collapsed configuration and in an expanded configuration;
wherein, in the expanded configuration, a central portion of the upper frame element is separated from a central portion of the lower frame element by an upper-to-lower dimension and the first side of the frame is separated from the second side of the frame by a side-to-side dimension; and
wherein, in the collapsed configuration, the upper frame element deforms at one or more regions between the anterior portion and the posterior portion of the first side of the frame, the upper frame element deforms at one or more regions between the anterior portion and the posterior portion of the second side of the frame, the lower frame element deforms at one or more regions between the anterior portion and the posterior portion of the first side of the frame, the lower frame element deforms at one or more regions between the anterior portion and the posterior portion of the second side of the frame, the upper-to-lower dimension is reduced, and the posterior frame element deforms to reduce the side-to-side dimension.

2. The device of claim 1, wherein:
a width of the first generally horizontal portion defines an upper anterior width,
a first distance between the first side and the second side defines an upper posterior width; and
the upper posterior width is at least about 40% larger than the upper anterior width.

3. The device of claim 1,
wherein the upper frame element includes a first thickness that decreases between the first connection and a first particular region that is located between the first connection and a central portion of the upper frame element; and
wherein the first thickness increases between the first particular region and a second particular region that is located between the first particular region and the central portion of the upper frame element; and
wherein, in the collapsed configuration, the upper frame element deforms at the first particular region.

4. The device of claim 3,
wherein the upper frame element includes a second thickness that decreases between the second connection and a third particular region that is located between the second connection and the central portion of the upper frame element; and
wherein the second thickness increases between the third particular region and a fourth particular region that is located between the third particular region and the central portion of the upper frame element; and
wherein, in the collapsed configuration, the upper frame element deforms at the third particular region.

5. The device of claim 3,
wherein the lower frame element includes a third thickness that decreases between the first connection and a fifth particular region that is located between the first connection and a central portion of the lower frame element;
wherein the third thickness increases between the fifth particular region and a sixth particular region that is located between the fifth particular region and the central portion of the lower frame element;
wherein the lower frame element includes a fourth thickness that decreases between the second connection and a seventh particular region that is located between the second connection and the central portion of the lower frame element; and
wherein the fourth thickness increases between the seventh particular region and a eighth particular region that is located between the seventh particular region and the central portion of the lower frame element; and
wherein, in the collapsed configuration, the lower frame element deforms at the fifth particular region and the seventh particular region.

6. The device of claim 1, further comprising a tongue guard disposed at least partially on the posterior frame element, the tongue guard comprising sheath that is closed at an anterior end and open at a posterior end.

7. The device of claim 1, wherein the upper frame element includes a bumper, the bumper including an enlarged portion of the upper frame element compared to an adjacent portion of the upper frame element.

8. The device of claim 7, wherein the bumper is located at least partially on the anterior portion of the upper frame element.

9. The device of claim 7, wherein a central portion of the upper frame element includes a lip protecting member.

10. The device of claim 9, wherein the lip protecting member includes a portion of a lock into which a corresponding feature of the lower frame element is configured to be positioned to lock the lower frame element relative to the upper frame element in the collapsed configuration.

11. A cheek and lip expansion device, the device comprising:
an upper frame element that extends between a first side of a frame and a second side of the frame, the upper frame element including a first thickness that decreases between the first side and a first particular region that is located between the first side and a central portion of the upper frame element, the first thickness increases between the first particular region and a second particular region that is located between the first particular region and the central portion of the upper frame element, the first side of the upper frame element bending posteriorly, the second side of the upper frame element bending posteriorly; and
a lower frame element that extends between the first side of the frame and the second side of the frame, the lower frame element including a second thickness that decreases between the first side and a third particular region that is located between the first side and a central portion of the lower frame element, the second thickness increases between the third particular region and a fourth particular region that is located between the third particular region and the central portion of the lower frame element, the first side of the lower frame element bending posteriorly, the second side of the lower frame element bending posteriorly, the first side of the upper frame element posteriorly connected to the first side of the lower frame element, the second side of the upper frame element posteriorly connected to the second side of the lower frame element,
wherein:
the device is selectively positionable in a collapsed configuration and in an expanded configuration,
in the expanded configuration, the central portion of the upper frame element is separated from the central portion of the lower frame element by an upper-to-lower dimension, and
in the collapsed configuration, the upper frame element deforms at the first particular region and the lower frame element deforms at the third particular region such that the upper-to-lower dimension is reduced.

12. The device of claim 11, wherein:
the upper frame element includes a first generally horizontal portion that includes the central portion of the upper frame element;
the first generally horizontal portion bends posteriorly to meet the first side and the second side; and
the upper frame element increases in width as it extends from the first generally horizontal portion to the first side and the second side.

13. The device of claim 12, wherein:
a width of the first generally horizontal portion defines an anterior width;
a distance between the first side and the second side defines a posterior width; and
the posterior width is at least about 40% larger than the anterior width.

14. The device of claim 12, further comprising a bumper of the upper frame element, the bumper including an enlarged portion of the upper frame element compared to an adjacent portion of the upper frame element, wherein the bumper is located at least partially on the generally horizontal portion of the upper frame element.

15. The device of claim 12, further comprising a lip protecting member of the central portion of the upper frame element, the lip protecting member being located anterior of the generally horizontal portion.

16. The device of claim 15, wherein the lip protecting member includes a portion of a lock into which a corresponding feature of the lower frame element is configured to be positioned to lock the lower frame element relative to the upper frame element in the collapsed configuration.

17. The device of claim 11, further comprising a posterior frame element that extends from the first side to the second side, the posterior frame element being connected to the upper frame element and the lower frame element at the first side and the second side.

18. The device of claim 17, wherein in the collapsed configuration, the posterior frame element is deformed such that a distance between the first side and the second side is decreased and dimensions of the device are reduced relative to the expanded configuration in at least two dimensions.

19. A cheek and lip expansion device comprising:
an upper frame element including a first side and a second side, the first side and the second side of the upper frame element including posteriorly extending portions;
a lower frame element including a first side and a second side, the first side and the second side of the lower frame element including posteriorly extending portions, a posterior portion of the first side of the upper frame element connected to a posterior portion of the first side of the lower frame element, a posterior portion of the second side of the upper frame element connected to a posterior portion of the second side of the lower frame element; and
a posterior frame element extending between the first side of the frame and the second side of the frame;
wherein:
the upper frame element includes a central generally horizontal portion that posteriorly bends, the upper frame element including a first thickness that decreases between a posterior portion of the first side of the frame and a first particular region that is located between the posterior portion of the first side of the frame and the central portion of the upper frame element, the first thickness increases between the first particular region and a second particular region that is located between the first particular region and the central portion of the upper frame element, and a second thickness that decreases between a posterior portion of the second side of the frame and a third particular region that is located between the posterior portion of the second side of the frame and the central portion of the upper frame element, the second thickness increases between the third particular region and a fourth particular region that is located between the third particular region and the central portion of the upper frame element;
the lower frame element includes a central generally horizontal portion that posteriorly bends, the lower frame element including a third thickness that decreases between a posterior portion of the first side of the frame and a fifth particular region that is located between the posterior portion of the first side of the frame and the central portion of the lower frame element, the third thickness increases between the fifth particular region and a sixth particular region that is located between the fifth particular region and the central portion of the lower frame element, and a fourth thickness that decreases between a posterior portion of the second side of the frame and a seventh particular region that is located between the posterior portion of the second side of the frame and the central portion of the lower frame element, the fourth thickness increases between the seventh particular region and a eighth particular region that is located between the seventh particular region and the central portion of the lower frame element; and the device is selectively positionable in a collapsed configuration and in an expanded configuration;

in the expanded configuration, the central portion of the upper frame element is separated from the central portion of the lower frame element by an upper-to-lower dimension and the first side of the frame is separated from the second side of the frame by a side-to-side dimension; and in the collapsed configuration, the upper frame element and the lower frame element deform at one or more regions such that the upper-to-lower dimension is reduced, and the posterior frame element deforms to reduce the side-to-side dimension.

20. The device of claim 19, wherein:

a width of the central generally horizontal portion of the upper frame element defines a first anterior width;

a width of the central generally horizontal portion of the lower frame element defines a second anterior width;

a distance between the posterior portion of the first side of the upper frame element or the lower frame element and the posterior portion of the second side of the upper frame element or the lower frame element defines a posterior width; and the posterior width is at least about 40% larger than the first anterior width and is at least about 40% larger than the second anterior width.

* * * * *